(12) United States Patent
Epstein et al.

(10) Patent No.: US 6,259,945 B1
(45) Date of Patent: Jul. 10, 2001

(54) METHOD AND DEVICE FOR LOCATING A NERVE

(75) Inventors: Richard Epstein, Sharon; David G. Abichaker, Boston, both of MA (US)

(73) Assignee: UroMed Corporation, Norwood, MA (US)

( * ) Notice: Subject to any disclaimer, the term of this patent is extended or adjusted under 35 U.S.C. 154(b) by 0 days.

(21) Appl. No.: 09/303,501

(22) Filed: Apr. 30, 1999

(51) Int. Cl.[7] ..................................................... A61B 5/05
(52) U.S. Cl. ............................................. 600/547; 600/554
(58) Field of Search .................................. 600/547, 548, 600/554; 606/32; 604/116

(56) References Cited

U.S. PATENT DOCUMENTS

| 5,284,153 | 2/1994 | Raymond et al. |
| 5,284,154 | 2/1994 | Raymond et al. |
| 5,775,331 | 7/1998 | Raymond et al. |
| 5,797,854 | * 7/1999 | Hedgecock ............................ 600/554 |
| 5,830,151 | * 11/1998 | Hadzic et al. ........................ 600/554 |
| 5,928,158 | * 7/1999 | Aristides ............................... 600/547 |

FOREIGN PATENT DOCUMENTS

| 0 298 268 | 6/1988 | (DE) . |
| 0876791 A1 | 11/1998 | (EP) . |
| WO 97/49452 | 12/1997 | (WO) . |

* cited by examiner

*Primary Examiner*—George Manuel
(74) *Attorney, Agent, or Firm*—Sterne, Kessler, Goldstein & Fox, P.L.L.C.

(57) ABSTRACT

An improved method and device for locating a nerve based on a closed-loop automated system is described. The device applies an electro-stimulus to a target tissue area and measures and interprets a change in a response evoked by application of an electro-stimulus to determine the location and responsiveness of a nerve. The improvement of the invention comprises a method for determining if the signal of the response is stable prior to application of electro-stimulation to prevent misinterpretation of a response and to enhance the locating accuracy of the device.

37 Claims, 17 Drawing Sheets

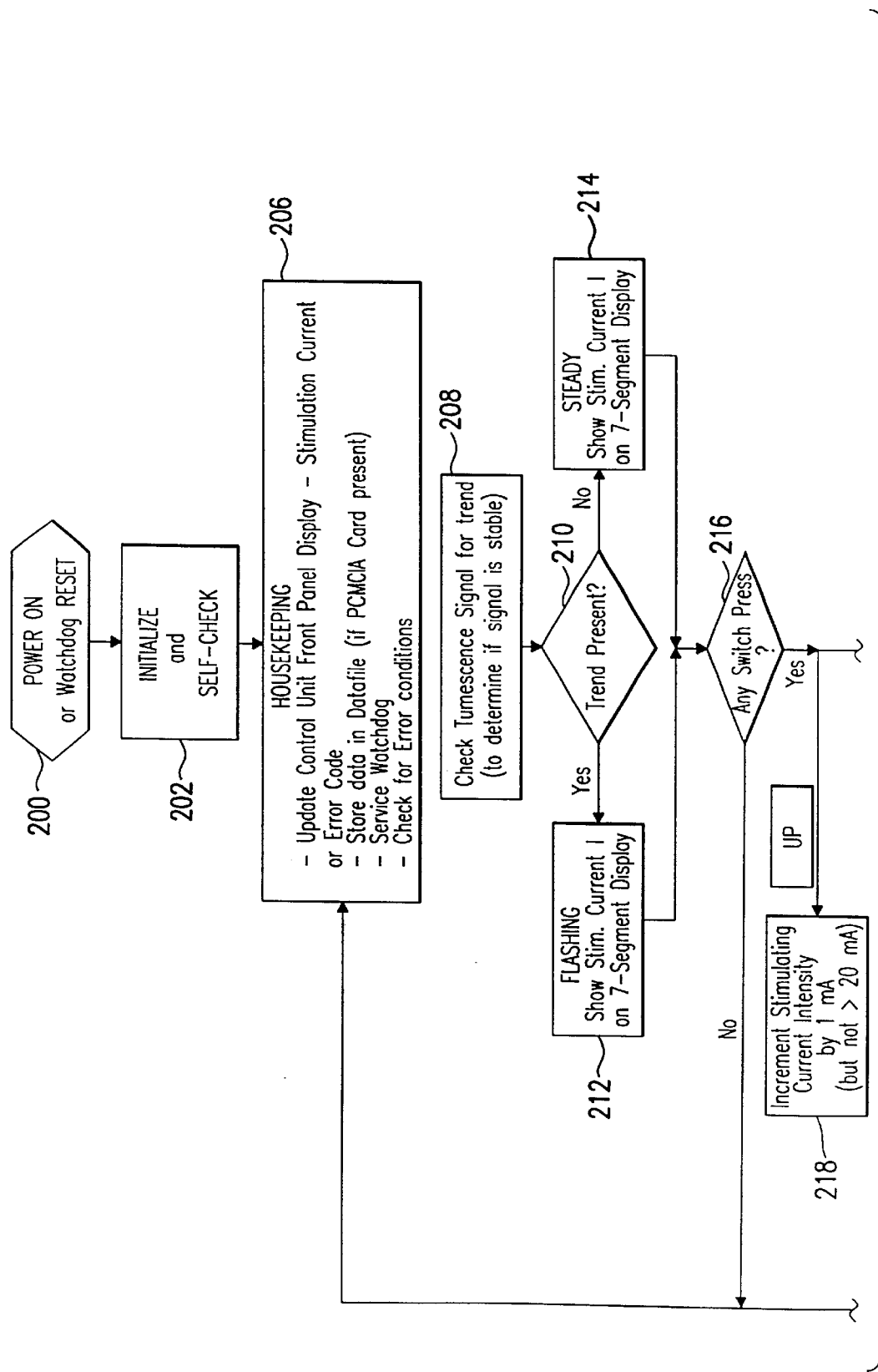

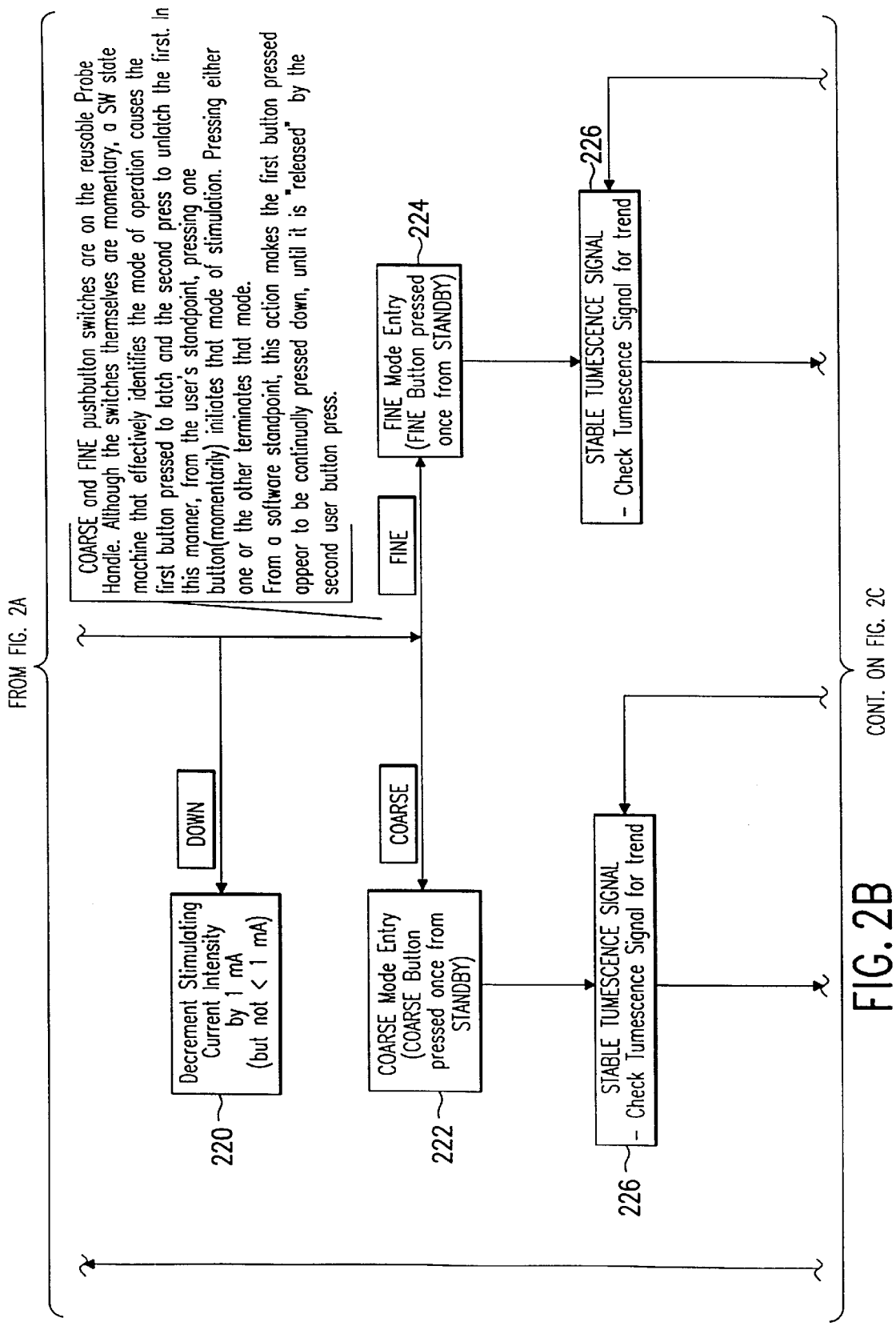

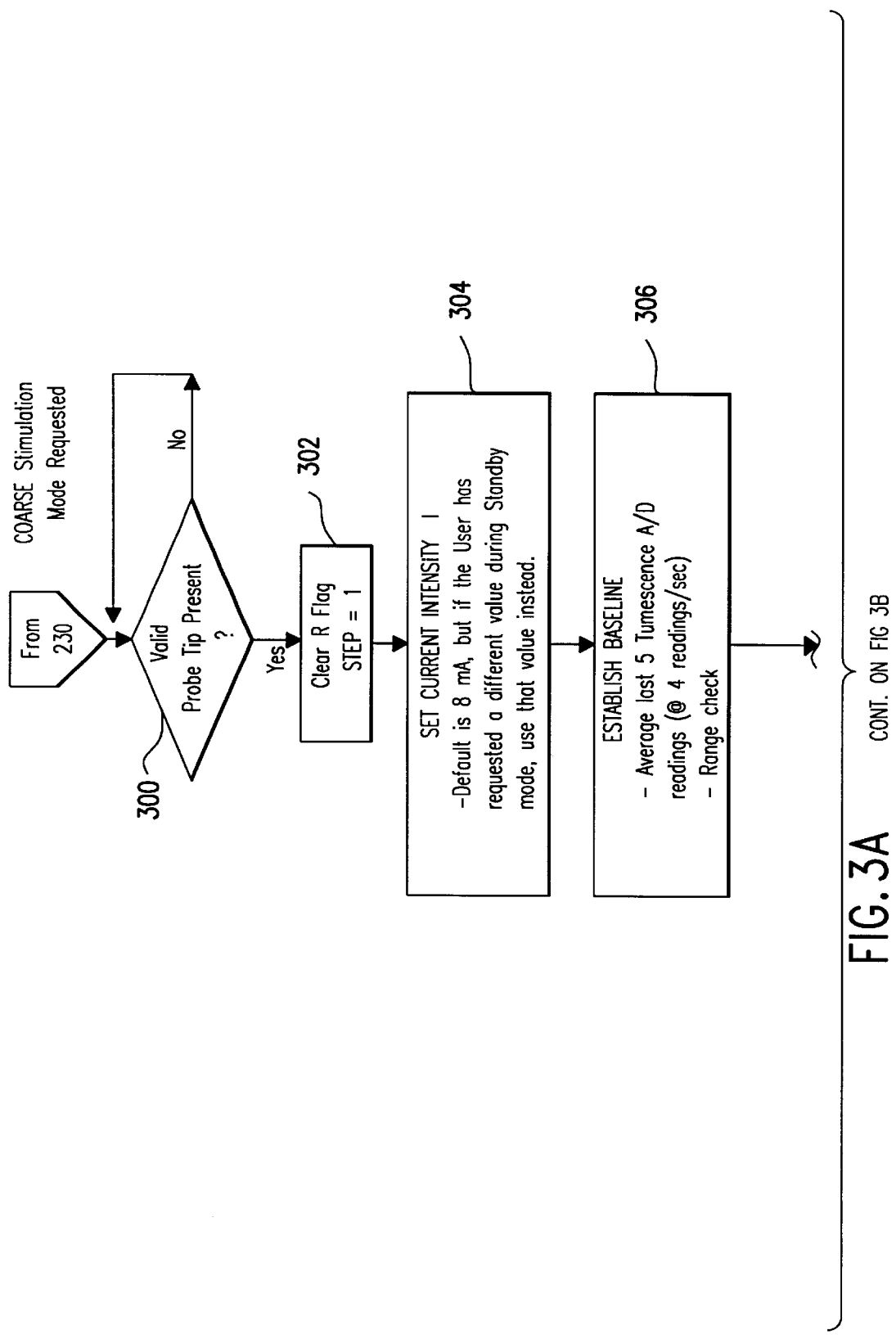
FIG. 3A  CONT. ON FIG 3B

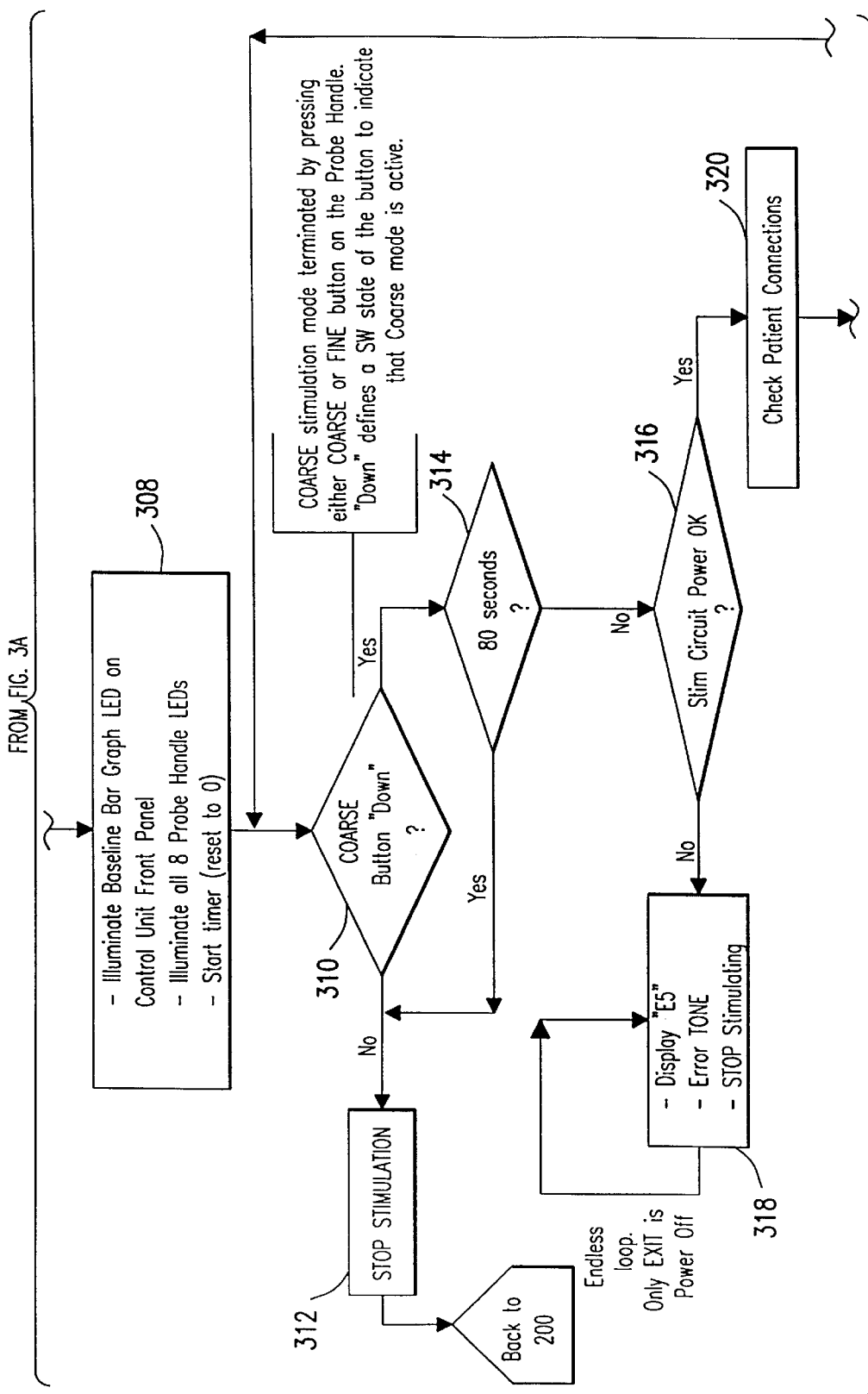
FIG. 3B  CONT. ON FIG. 3C

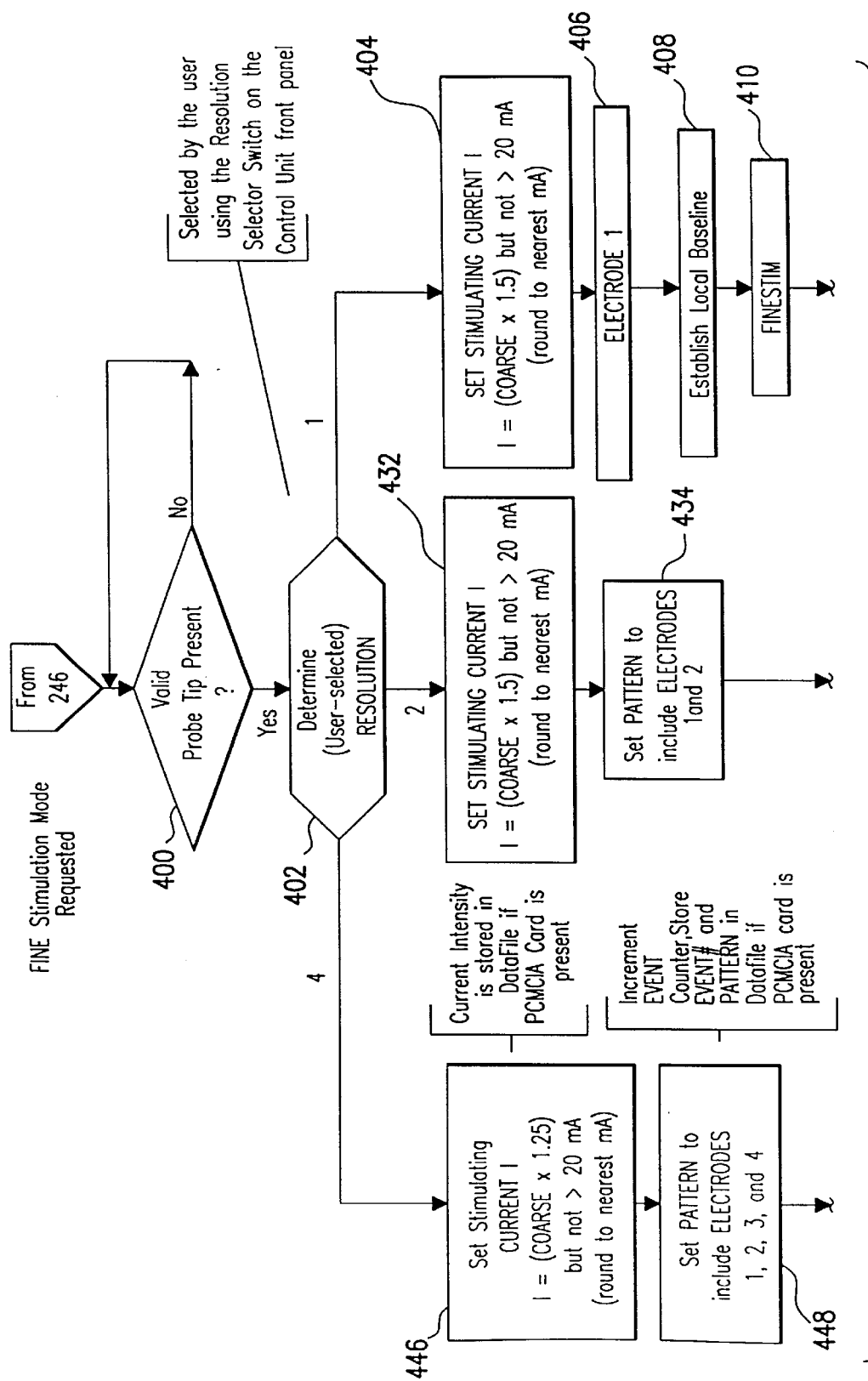
FIG. 4A  CONT. ON FIG. 4B

Algorithm for determining the stability of the Tumescence signal.

T = The sampling time (Currently = 5 sec, but could be programmed to be any time)
K = The sample size of each data point (currently = 5)
σ = Standard deviation of pue error which is free of trend (currently @ 7.6 AD units)
CRIT-L = The critical value of the Linear Chi square distribution ($\chi_l^2$)
CRIT-Q = The critical value of the Quadratic Chi square distribution ($\chi_q^2$)
CRIT-C = The critical value of the Cubic Chi square distribution ($\chi_c^2$)
$X_{li}$ = Coded linear contrast coefficient (currently = -3, -1, 1, 3)
$X_{qi}$ = Coded quadratic contrast coefficient (currently = 1, -1, -1, 1)
$X_{ci}$ = Coded cubic contrast coefficient (currently = -1, 2, -3, 1)
$Y_1, Y_2, Y_3, Y_4$ = Averages of data points of sample size set by K.

$$\text{Linear Chi square statistics} = \chi_l^2 = \frac{[\chi_{l1} Y_1 + \chi_{l2} Y_2 + \chi_{l3} Y_3 + \chi_{l4} Y_4]^2}{\sigma^2 [\chi_{l1}^2 + \chi_{l2}^2 + \chi_{l3}^2 + \chi_{l4}^2]}$$

$$\text{Quadratic Chi square statistics} = \chi_q^2 = \frac{[\chi_{q1} Y_1 + \chi_{q2} Y_2 + \chi_{q3} Y_3 + \chi_{q4} Y_4]^2}{\sigma^2 [\chi_{q1}^2 + \chi_{q2}^2 + \chi_{q3}^2 + \chi_{q4}^2]}$$

$$\text{Cubic Chi square statistics} = \chi_c^2 = \frac{[\chi_{c1} Y_1 + \chi_{c2} Y_2 + \chi_{c3} Y_3 + \chi_{c4} Y_4]^2}{\sigma^2 [\chi_{c1}^2 + \chi_{c2}^2 + \chi_{c3}^2 + \chi_{c4}^2]}$$

If $\chi_l^2$, $\chi_q^2$, or $\chi_c^2$ are $\geq$ then CRIT-L, CRIT-Q or CRIT-C respectively, then a statistically significant trend exists in the signal indicating that the signal is not stable.

FIG. 6

METHOD AND DEVICE FOR LOCATING A NERVE

BACKGROUND OF THE INVENTION

1. Field of the Invention

The present invention relates to a method and device for locating a nerve. More particularly, the present invention is a method and device for locating the carvernosal nerve having means for determining the stability of a tumescence signal to prevent misinterpretation of a response to application of an electro-stimulus.

2. Related Art

The technique of applying an electro-stimulus to an area of tissue to locate a nerve for the purpose of administering anesthesia or to avoid severing a nerve during the sectioning or excision of tissue has been practiced for decades. Conventional devices for applying an electro-stimulus to an area of tissue have taken the form of an insulated hypodermic needle coupled to an electrical current. In an attempt to locate the nerve, the needle was placed within a tissue site believed to contain the nerve and a pulse of electrical current was applied to the tissue. The effectiveness of each pulse was established by visually inspecting the associated organ or muscle for a response or by taking a report of paresthesia offered by the patient. After evaluating the effectiveness of a pulse of electrical current, the operating physician repositioned the needle and modified the intensity of the next pulse to be applied to the tissue based on his evaluation of the response to the previous pulse. The steps were continued until the operating physician believed the needle to be proximate to the nerve to be located (typically, when a low intensity pulse evoked a strong, immediate response in the associated organ or muscle). While such a device was effective at applying a pulse of electrical current to evoke some type of response, actual localization of the nerve using the afore-described technique was slow and imprecise because the success of the technique was totally dependent on the skill of the operating physician who was responsible for performing each one of the steps.

Localization of a nerve by conventional electro-stimulation is particularly complicated if the nerve comprises multiple, microscopic branches or if the nerve is disposed in a region of the body difficult to reach in light of the surrounding anatomy. Still other nerves, such as autonomic nerves, can be difficult to locate due to the fact that such nerves evoke response patterns which cannot be immediately observed or interpreted by the operating physician administering the electro-stimulus to the tissue site. For example, stimulation of the carvernosal nerve evokes a multi-stage response comprising 1) relaxation of the smooth muscles of the arterioles supplying the penis, 2) dilation of the arteries leading to the penis, 3) constriction of the veins carrying blood away from the penis, and 4) accumulation of blood in the cavernosa. Such a multi-stage response is especially difficult to interpret because the response might not occur until some time after application of the stimulus, perhaps as long as two or more seconds. Given the afore-described factors, it is difficult for an operating physician to determine the location of a nerve via observation of the response pattern alone.

In an effort to reduce the role of the operating physician, and to accommodate the afore-described factors associated with complex or autonomic nerves, attempts have been made to fully automate a nerve locating device. A partially automated device specifically structured to assist in locating the carvernosal nerve is disclosed and claimed in U.S. Pat. Nos. 5,284,153 and 5,284,154 to Raymond et al. The device comprises a stimulating probe, a response detecting means for detecting and measuring tumescence, and a control means comprising means for automatically modulating the intensity of a stimulus to be applied to the tissue believed to contain the carvernosal nerve. With the device, the operating physician positions the stimulating probe beneath the tissue to be stimulated. A stimulus of a pre-determined intensity is applied to the tissue and the response detecting means detects and measures a tumescence response. The stimulating probe is re-positioned by the operating physician and the intensity of the next stimulus to be applied to the tissue is modulated by the automatic modulating means based on an evaluation of the intensity of the tumescence response by the control means. The steps are repeated until the automatic stimulus modulating means of the device converges to a stimulus intensity known to successfully stimulate the carvernosal nerve when the stimulating probe is within 0.5 mm of the nerve.

In an attempt to reduce reliance on the skill of the surgeon, Raymond et al. developed a closed-loop system for locating a nerve, particularly the carvernosal nerve. U.S. Pat. No. 5,775,331 discloses an apparatus and method for locating the carvernosal nerve comprising a stimulating probe having an electrode array, an automatic control means, and a tumescence response detecting means. With the device of U.S. Pat. No. 5,775,131 a stimulus is applied to a target area of tissue by the electrode array of the stimulating probe. The response detecting means records the tumescence response and the control means automatically modifies the stimulus application site and the intensity of the next stimulus to be applied to the target tissue area based on the evaluation of the tumescence response. The method is repeated until the nerve is located.

Through use of the device of U.S. Pat. No. 5,775,331, it has been discovered that other aspects of the nerve locating technique or the surgical method can induce detectable changes in a tumescence signal which can reduce the accuracy of the device. For the carvernosal nerve, for example, it has been determined that physical manipulation of the tumescence monitor, a change in the patient's blood pressure, loss of blood during surgery, the level and type of anesthesia, or natural changes in penile tumescence can evoke a change in the tumescence signal which interferes with the device's ability to accurately locate the nerve. Furthermore, the response to stimulation for some visceral or autonomic nerves (such as the carvernosal nerve) may persist for several seconds after cessation of successful stimulation and, in some cases, refractory responses may follow an initial response to successful stimulation.

Thus, there is a need for a device for locating a nerve which is closed-loop (and, thus, independent of the skill of the operator) and comprises means for determining if a signal from a nerve fiber, organ or muscle is stable prior to application of an electro-stimulus to avoid misinterpretation of a response to electro-stimulation.

SUMMARY OF THE INVENTION

It was with the preceding needs in mind that the present invention was developed. The present invention is an improvement to the Apparatus and Method for Locating a Nerve disclosed and claimed in U.S. Pat. No. 5,775,331 to Raymond el al. The improvement resides in a means for analyzing if a signal (particularly, a tumescence signal) is stable prior to application of electro-stimulation to prevent misinterpretation of a change in the signal. The analysis for determining if the signal is stable is based on a mathematical multi-order analysis.

In one aspect, the present invention is a device for stimulating and locating the carvernosal nerve comprising means for detecting and measuring a tumescence signal and a change in the tumescence signal, means for determining the stability of the tumescence signal provided by the signal detecting and measuring means, means for applying an electro-stimulus to a plurality of sites within an area of tissue likely to contain the carvernosal nerve, means for interpreting the change in the tumescence signal evoked by application of an electro-stimulus to determine the location of the nerve, means for automatically modifying the stimulus application site, and means for indicating the location of the carvernosal nerve to the user. The determining means characterizes the tumescence signal as unstable if the signal exhibits a trend value which is greater than a predetermined threshold value.

The device further comprises means to prevent the applying means from applying an electro-stimulus when the determining means has characterized the tumescence signal as unstable. The device further comprises means for indicating to the user that the determining means has determined that the tumescence signal is unstable. The device further comprises memory for storing a library of predetermined threshold values for determining the stability of the tumescence signal by the determining means.

The automatic modifying means automatically modifies the stimulus application site based on an interpretation of the change in the tumescence signal evoked by application of the electro-stimulus. The applying means comprises an array of electrodes. The automatic modifying means modifies the stimulus application site in accordance with an electrode activating algorithm and a current intensity variation algorithm. The tumescence signal detecting and measuring means comprises a tumescence monitor.

In another aspect, the invention is a method for locating the carvernosal nerve, comprising the steps of detecting and measuring a tumescence signal, determining the stability of the tumescence signal and characterizing the signal as stable or unstable, applying an electro-stimulus to a tissue site likely to contain the nerve if it is determined that the tumescence signal is stable, detecting and measuring a change in the tumescence signal evoked by application of the electro-stimulus, and interpreting the change in the tumescence signal evoked by application of the electro-stimulus. The method further comprises the step of characterizing the tumescence signal as unstable if the signal exhibits a trend value which is greater than a predetermined threshold value. The step for determining if the tumescence signal is stable or unstable comprises a mathematical, multi-order analysis.

The method further comprises the step of automatically modifying the stimulus application site based on the interpretation of the change in the tumescence signal. The method further comprises the step of indicating when the determining step has determined that the tumescence is unstable.

In still another aspect, the invention is a method for determining the stability of a change in a signal from a nerve fiber, organ or muscle, comprising the step of recording and analyzing a contrast value of the signal at discrete intervals.

BRIEF DESCRIPTION OF THE FIGURES

Various objects, features and attendant advantages of the present invention can be more fully appreciated and understood from the following detailed description of the present invention when considered in connection with the accompanying figures, in which:

FIG. 6 illustrates the mathematical equations for determining the stability of a signal.

DETAILED DESCRIPTION OF THE PREFERRED EMBODIMENTS

As discussed above, the present invention is an improvement of the device and method for locating a nerve disclosed and claimed in U.S. Pat. No. 5,775,331 to Raymond et al. Prior to discussing the method of the improvement of the present invention, the structure of the device will be described with particular reference to the accompanying figures and to the disclosure of U.S. Pat. No. 5,775,331 to Raymond el al. Although reference is made to specific sections, the disclosure of the '331 patent is incorporated herein, in its entirety, by reference.

Figure 1:
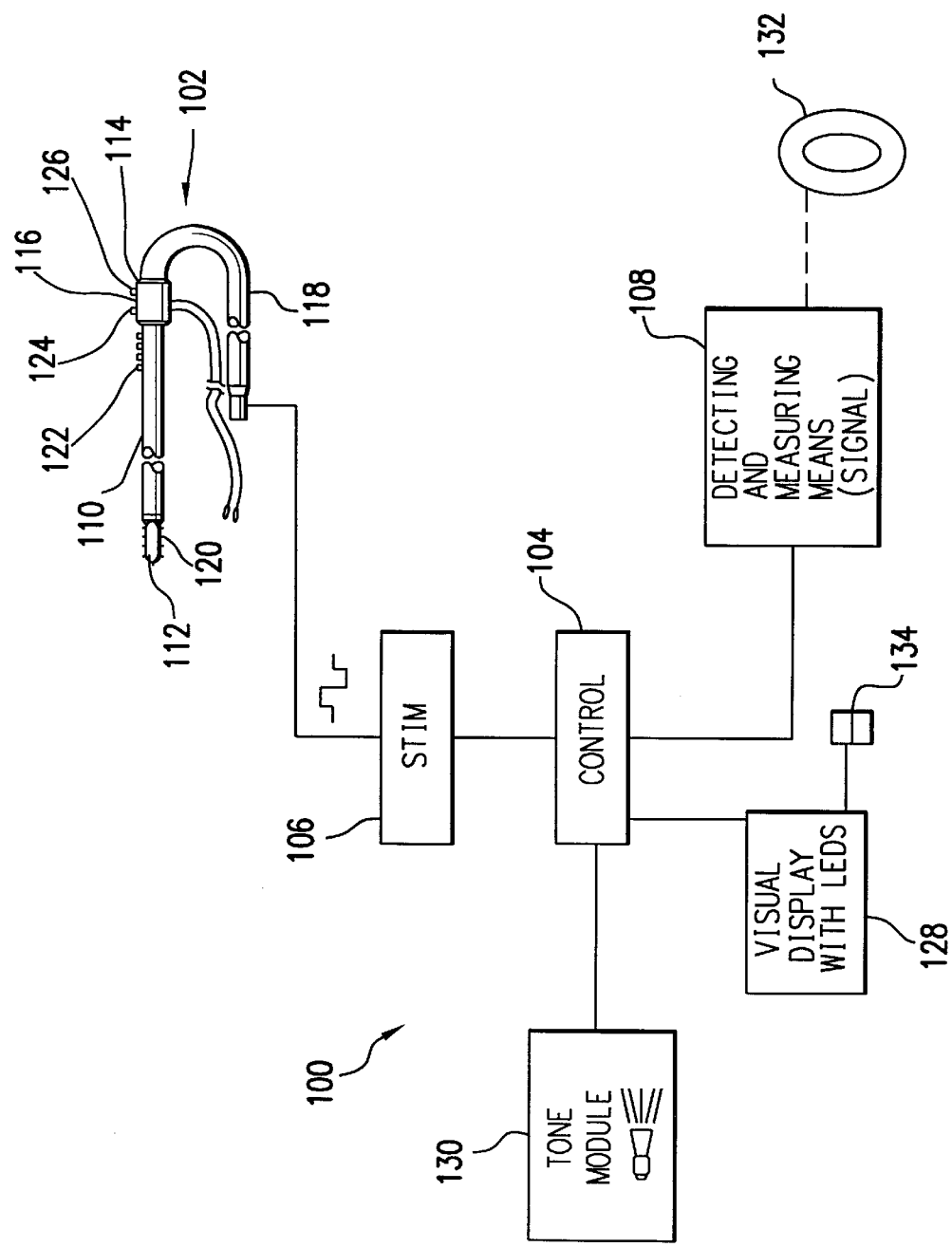
FIG. 1 is a schematic of the components of the device of the present invention.

With reference now to FIG. 1 of the accompany drawings, device 100 comprises stimulus applying means 102, control means 104, a stimulating current circuit 106, and a signal and response detection means 108. In a preferred embodiment, stimulus applying means 102 is a probe 110 having a stimulating tip 112, a handle 114, a switch panel 116, and a cable 118 for connecting the probe to control means 104. Stimulating tip 112 comprises an array of electrodes 120 which delivers a current pulse (an electro-stimulus) to the area of tissue believed to contain the nerve to be located. The array preferably comprises eight electrodes; however, it should be realized by those skilled in the art that the stimulating tip of the probe could be provided with any number of electrodes (including only one) depending on the nerve to be located and the associated tissue area. Handle 114 is provided with light emitting diodes (LEDs) 122 which correspond in number and position to the array of electrodes disposed on stimulating tip 112. Switch panel 116 comprises switches 124 and 126 for activating and terminating the stimulating modes of the device to be discussed in more detail below. The electrodes of the probe are activated in accordance with an electrode activating algorithm discussed in more detail below with respect to FIGS. 4 and 5. A complete description of probe 110 and its structure and use appears in the figures and description of the '331 patent beginning at column 7, line 40 and in FIGS. 1, 2, 3A, 31B and 3C. Although probe 110 is preferred to stimulate and locate the carvernosal nerve, others devices capable of delivering an electro-stimulus to a target tissue area would be suitable.

Control means 104 comprises a computer having a central processing unit (CPU), logic circuitry, memory, peripheral controllers and drivers which utiliz data acquisition hardware and software. Control means 104 is structured and programmed to perform and control all operations of the device in accordance with a number of algorithms. Specifically, the hardware and software of control means 104 performs the signal analyzing and interpreting functions for locating the nerve discussed in more detail below. Control means 104 further comprises a visual display 128 with LEDs and an audible tone module 130 for visually displaying and audibly communicating data (such as the intensity of the electro-stimulus or information concerning the stability of a tumescence signal) to the user in an intelligible format. An "up" and "down" switch 134 is also provided to manually increase or decrease the intensity of the stimulating current, if desired.

Stimulating current circuit 106 generates and delivers a biphasic square to electrodes 120 of probe 110 in response to a trigger by control means 104. Delivery of a current pulse to a particular electrode of the array is accomplished by a set of relays activated in accordance with the electrode activation algorithm of the stimulating methods to be discussed in more detail below. A complete description of the stimulating current circuit of the device appears at column 9, lines 22–55 of the '331 patent.

With continuing reference to FIG. 1, a signal and response detection means 108 is provided to detect and measure a signal from a nerve fiber, organ or muscle and a change in the signal evoked by application of an electro-stimulus (also referred to as a response). Selection of a device to detect and measure a signal and response to application of an electro-stimulus is dependent upon the nerve to be located. For the carvernosal nerve, a tumescence monitor 132 comprising distensible tubing filled with a conductive fluid is preferable. However, any other device capable of detecting and measuring penile tumescence would accomplish the objectives of the present invention. Other devices for detecting and measuring penile tumescence or for detecting and measuring a signal and response in other nerves are disclosed in FIG. 4 of the drawings of the '331 patent and at column 11, lines 22–56.

Having described the structure of the device, the method of the present invention will now be described. In general, the method for locating a nerve comprises the steps of:

1. detecting and measuring a signal from a nerve fiber, tissue or organ;
2. determining the stability of the signal and characterizing the signal as "stable" or "unstable";
3. applying an electro-stimulus to a tissue site likely to contain the nerve to be located if it is determined that the signal is stable;
4. detecting and measuring a change in the signal (a response) evoked by application of the electro-stimulus;
5. interpreting the change in the signal (the response) evoked by application of the electro-stimulus;
6. modifying the intensity of the stimulus and the stimulus application site based on the interpretation of the response to determine the location of the nerve; and
7. indicating the location of the nerve.

In accordance with the method of the present invention, an electro-stimulus will not be applied until it is determined that the signal is stable. If the signal is unstable, the signal is continuously monitored until stability is established.

The method for determining if the signal is stable prior to application of an electro-stimulus is based on a mathematical, multi-order analysis. More particularly, the signal is analyzed for linear, cubic and quadratic "trends" indicative of an unstable signal (that is, an indication that a factor other an application of an electro-stimulus has caused a change in the signal which could result in an inaccurate assessment of the location of the nerve). The mathematical equations for determining the stability of the signal appear in FIG. 6 and a further discussion of the equations appears below.

Figure 2C:
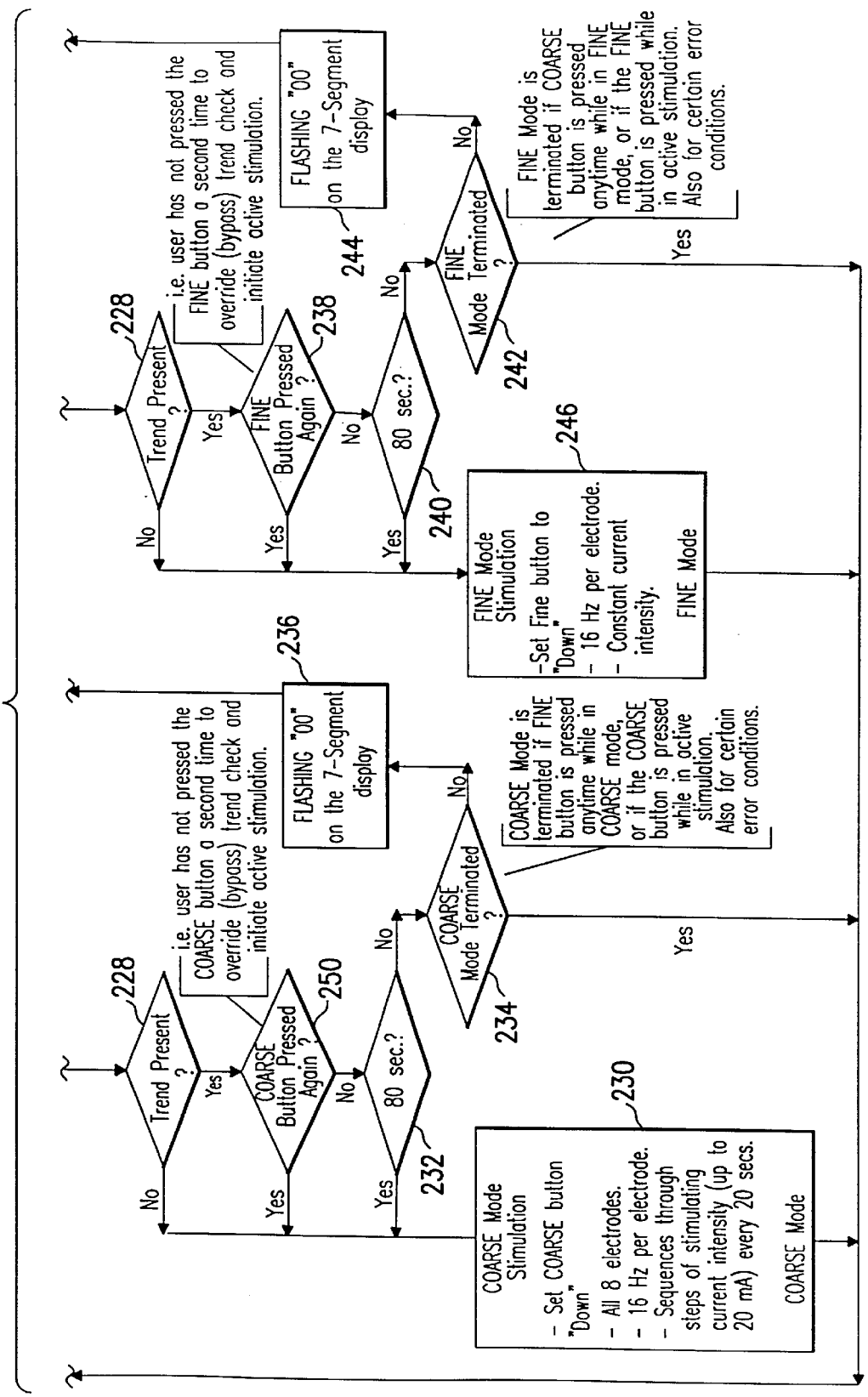
FIG. 2 is a flowchart illustrating the steps of the method for locating a nerve using the device of the present invention with particular reference to a method for determining the stability of a signal.

FIG. 2 of the accompanying drawings is a flowchart summarizing the method of operation of the device for locating the nerve. Although the accompanying figures are specific to localization of the carvernosal nerve, it should be understood by those skilled in the art that the methods illustrated therein can be practiced to locate any nerve. At the top of FIG. 2, block 200 powers up the device and the "watchdog" program resets the CPU of control means 104. The next step, shown as block 202 is an "initialize and self-check" step which initializes all of the device parameters and performs a diagnostic on the control means and remaining components of the device. A housekeeping step shown as block 206 follows the initialize and self-check step. During the housekeeping step, the front panel of visual display 128 is updated, data is stored in a datafile if a PCMCIA (Personal Computer Memory Card International Association) card is present, watchdog program is serviced, and the device is checked for error conditions. Next, the tumescence signal detected and measured by tumescence monitor 132 is analyzed for stability as shown by block 208. During this step of the method, the mathematical multi-order analysis of FIG. 6 is performed to determine if the signal is stable. More particularly, the tumescence signal is continuously monitored in discrete 5 second segments for the existence of a "trend" determined by analyzing the linear contrast, the cubic contrast, and the quadratic contrast of the signal. The signal is considered to be unstable (that is, a trend is considered to be present) if a contrast value is greater than its corresponding predetermined critical contrast value defined, respectively, as CRIT-L (the linear critical Chi square statistic), CRIT-C (the cubic critical Chi square statistic), and CRIT-Q (the quadratic critical Chi square statistic).

In one embodiment of the method for determining the stability of the signal, the signal is monitored its value is recorded and its linear, cubic, and quadratic contrasts values are recorded and analyzed against the CRIT-L, CRIT-C, and CRIT-Q parameters, respectively at intervals of 0.25 seconds for 5 seconds. If any one of the contrast values falls above its corresponding critical parameter (for example, if the cubic contrast value is greater than CRIT-C), the signal is considered to be unstable. The signal is continuously monitored and mathematically analyzed until it is determined that the signal is stable and that it is appropriate to proceed with application of electro-stimulation.

If decision block 210 determines that a trend is present, the intensity of the preset stimulating current flashes on visual display 128 of control means 104, indicating to the user that the signal is unstable and that it is not appropriate to proceed with application of electro-stimulation (block 212). If a trend is not present (that is, if the signal is determined to be stable), the intensity of the stimulating current is shown on the visual display of the control means by steady illumination, indicating that it is appropriate to proceed with application of electro-stimulation.

Decision block 216 determines if the user has pressed a switch on switch panel 116 of stimulating probe 110. The choices include pressing the up/down switch 134 on control means 104 to increase the intensity of the stimulating current by 1 mA (but not to an intensity greater than 20 mA) as shown by block 218, pressing the up/down switch on the control means to decrease the stimulating current by 1 mA (but not to an intensity less than 1 mA) as shown by block 220, pressing the course stimulation switch 124 on probe 110 as shown by block 222, or pressing the fine stimulation switch 126 on the probe as shown by block 224. If the answer is no, the method returns to step 206.

The stability of the tumescence signal is checked at block 226. If it is determined that the signal is stable (answer "no" to decision block 228) either coarse mode stimulation is activated as shown by block 230 or fine mode stimulation is activated as shown by block 246, depending on whether the coarse stimulation switch was pressed (block 222) or the fine stimulation switch was pressed (block 224). If it is determined that a trend is present and that the signal is unstable, decision block 250 determines if the coarse stimulation switch has been pressed to override or bypass the tumescence signal stability check. If the coarse stimulation switch has been pressed, the method proceeds to coarse mode stimulation (block 230). If the answer to decision block 250 is no, decision block 232 determines if the tumescence signal has been unstable for 80 seconds. If the answer to decision block 232 is no, and if the coarse stimulation mode is not terminated by pressing the course stimulation switch (that is, the answer to decision block 234 is also "no"), the visual display flashes "00" on the visual display of the control means to indicate to the user that the signal is not stable (block 236). If the answer to decision block 234 is yes (that is, coarse mode stimulation has been terminated by pressing the coarse mode stimulation switch), the method returns to housekeeping block 206. It should be noted that if the device indicates that the tumescence signal is unstable, the user can override or bypass the signal stability check and proceed to application of electro-stimulation by pressing the course or fine mode switch located on the probe handle. If the user chooses to heed the warning provided by the signal stability check, the method returns to block 206 and cycles through that portion of the method until the signal is stable.

If the fine mode stimulation switch has been pressed to bypass the tumescence signal stability check (that is, the answer to decision block 238 is "yes", the method proceeds to fine mode stimulation (block 246). If the answer to decision block 238 is no, decision block 240 determines if the tumescence signal has been unstable 80 seconds. If the answer to decision block 240 is no, and if the fine stimulation mode is not terminated by pressing the fine mode stimulation switch (that is, the answer to decision block 242 is no), the visual display flashes "00" on the visual display of the control means to indicate to the user that the signal is not stable (block 244). If the answer to decision block 242 is yes (that is, fine mode stimulation has been terminated by pressing the fine mode stimulation switch), the method returns to housekeeping block 206. By continuously monitoring the stability of the tumescence signal prior to application of an electro-stimulus, interpretation of a change in the signal (a response) to electro-stimulation is enhanced and, therefore, improves the utility and accuracy of the device.

Figure 3C:
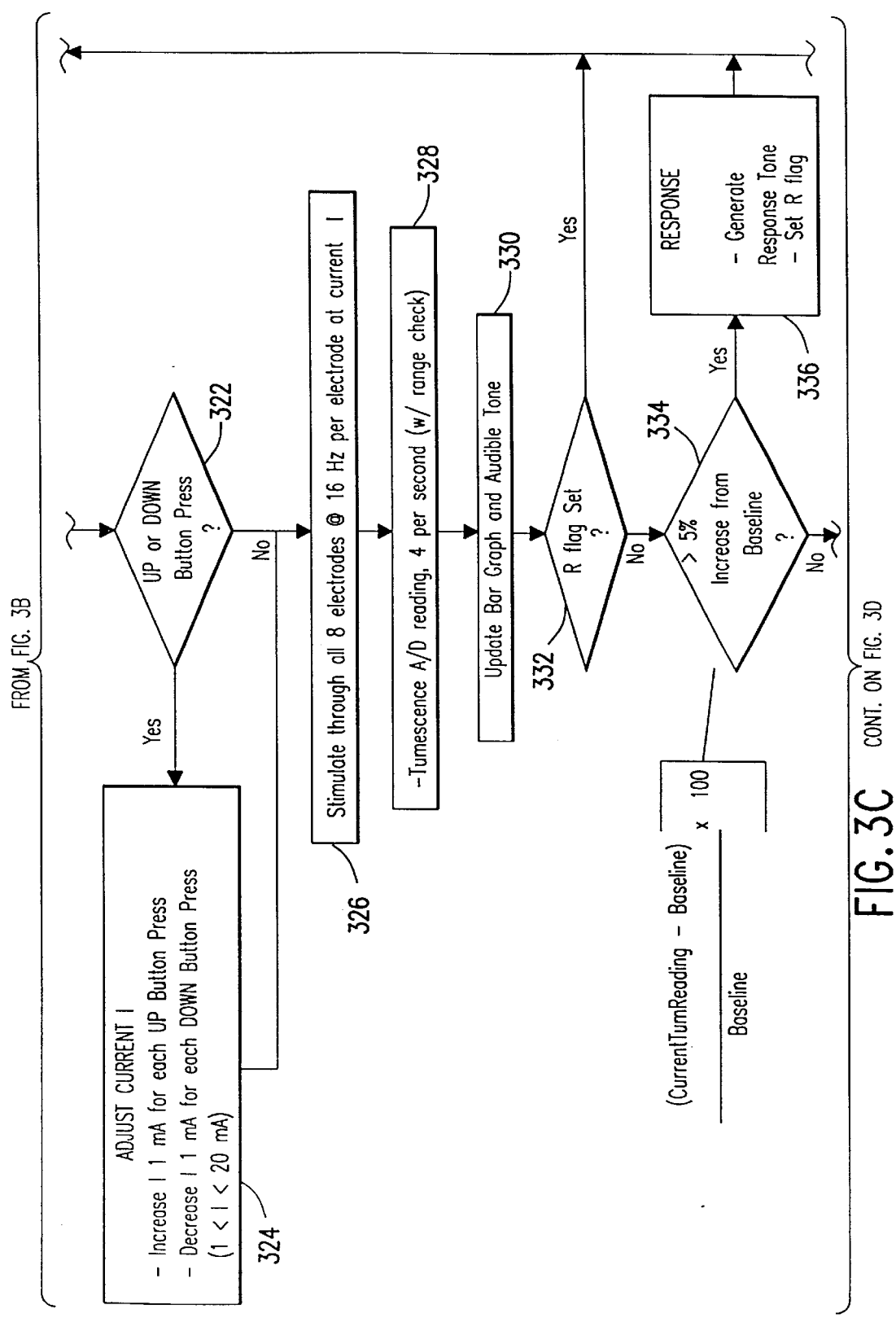
FIG. 3 is a flowchart illustrating a first method for stimulating the nerve known as the "coarse" stimulation mode.
Figure 3D:
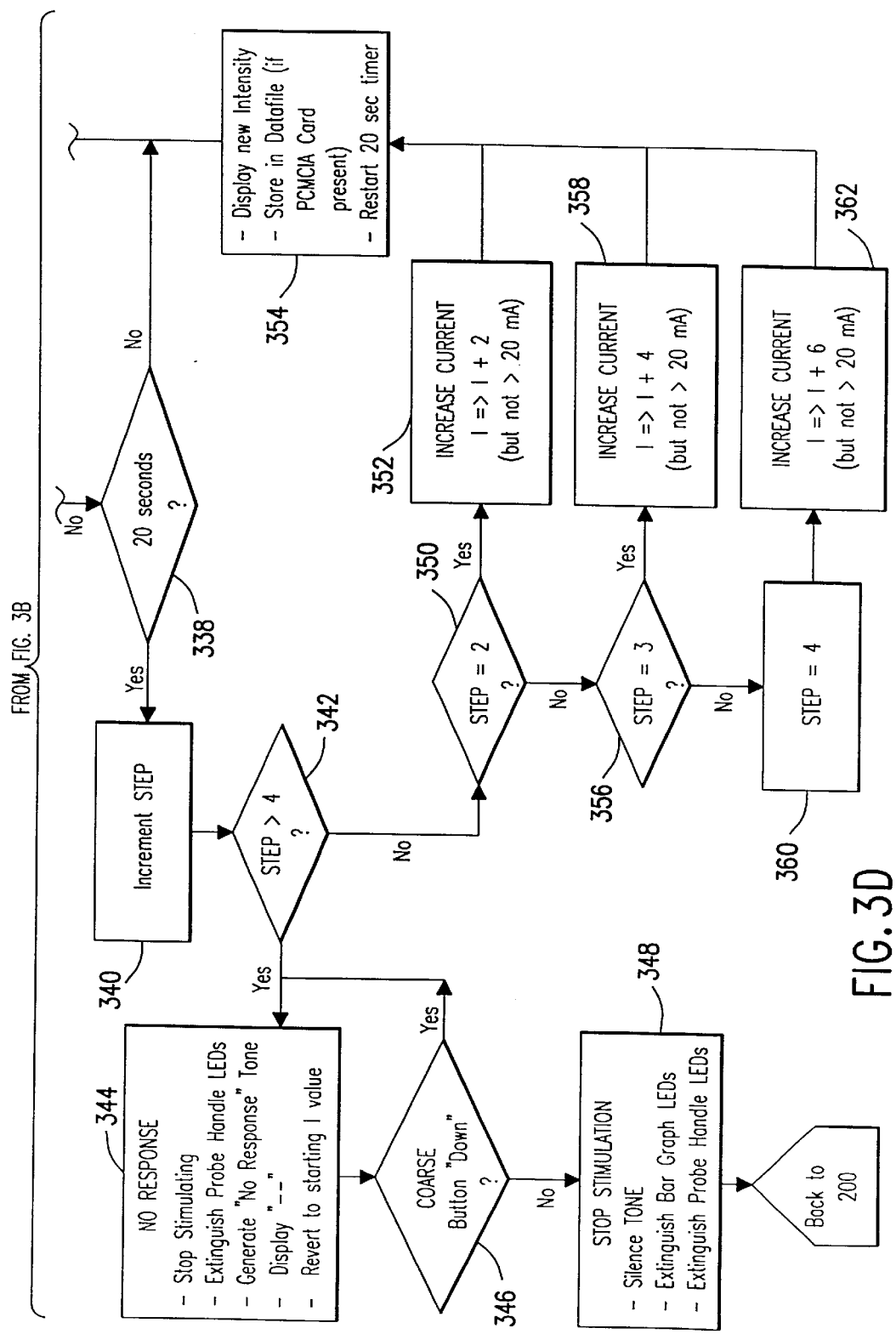

Having described the method for determining the stability of the tumescence signal prior to application of electro-stimulation, the course and fine modes of stimulation will now be described. With reference to FIG. 3, the coarse mode stimulation method for applying an electro-stimulus to a target tissue area is shown. In general, coarse mode stimulation entails application of an electro-stimulus by all eight electrodes of probe 110 at a frequency of 16 Hz. The device sequences through "steps" of electro-stimulation, each step having a duration of 20 seconds and an intensity of no more than 20 mA. The method starts at decision block 300 which determines if a valid probe 110 is present. If a valid probe is present, the response flag is cleared at block 302 and the STEP 1 electro-stimulation sequence is called. Block 304 defaults the intensity I of the stimulating current pulse to 8 mA. However, the user has the option of requesting another intensity value, if desired as shown at 218 and 220 in FIG. 2. A check is then made of the tumescence signal range to determine if the current tumescence signal is within an acceptable range (preferably, greater than 0 V and but less than approximately 4.5 V). If the tumescence signal is too high or too low to allow proper operation of the device, an error code is displayed on visual display 128 of the device. After completing a check of the range of the tumescence signal, block 306 establishes a baseline value for the tumescence signal by averaging the last 5 tumescence signal readings at a rate of 4 signal readings per second. Block 308 then displays the tumescence signal baseline value on visual display 128 of the control means, illuminates LEDs 122 of handle 114, and starts the timer of the control means by resetting it to 0. If decision block 310 determines that the coarse mode switch has been pressed again (returning the switch to the up position), stimulation is terminated at block 312 and the method returns to block 202 of method illustrated in FIG. 2. If decision block 310 determines that the coarse stimulation switch is down (that is, coarse mode stimulation is active), block 314 determines if 80 seconds has elapsed. If the answer to decision block 314 is yes, coarse mode stimulation is terminated at block 312. If the answer to decision block 314 is no, decision block 316 determines if power is being supplied to stimulating current circuit 106. If the answer to block 316 is no, block 318 displays an error code on the visual display and the device enters an endless loop which can be exited only by turning the power off. If power is being supplied to the stimulating current circuit 106, the patient connections to tumescence monitor 132 are checked at block 320. Next, block 322 determines if the up/down switch on control means 104 has been pressed to increase or decrease the intensity of the electro-stimulus. If the answer to decision block 322 is yes, block 324 determines the intensity of the stimulating current as adjusted by the user. Each press on the up button increases the intensity I of the electro-stimulus by 1 mA. Each press on the down button decreases the intensity I by 1 mA. Block 326 stimulates through all 8 electrodes of probe 110 in a predetermined sequence at a frequency of 16 Hz and at intensity I (as determined by block 324) or at the original default intensity of 8 mA. Block 328 performs another tumescence signal range check at a rate of 4 tumescence signal readings per second. Block 330 performs an update to the visual and audible display of the control means to indicate the baseline tumescence signal value. Next, block 332 determines if a response flag R has been set. If the answer is yes, the method returns to decision block 310. If the answer is no, decision block 334 determines if the tumescence response has increased at least 5% from baseline. If the answer to block 334 is yes, a response tone is generated by audible tone module 130 and a response flag R is set at block 336. Once flag R is set, the current is maintained at a constant intensity through the rest of the stimulation mode. The method returns to decision block 310 and repeats. If the answer to decision block 334 is "no" decision block 338 determines if 20 seconds has elapsed. If the answer to the 20 second decision block 338 is no, the method returns to decision block 310 and repeats. If the answer to block 338 is yes, block 340 calls for the INCRE- MENT STEP step. Decision block 342 determines if the intensity I has been increased over 4 stimulating steps or cycles of the coarse stimulation mode. If the device has already cycled through 4 stimulating steps (increasing the stimulus intensity by 2 mA per each successive step), block 344 establishes that no response has been evoked and it extinguishes LEDs 122 on probe 110. Audible tone module 130 generates a no-response tone and the device reverts to the starting stimulating current intensity I established at block 304. If the coarse stimulation button is pressed (coarse mode stimulation active) at decision block 346, the method returns to block 344. If the coarse stimulation button has not been pressed, block 348 silences the audible tone and extinguishes the data on visual display 128. If the answer to decision block 342 is no, decision block 350 determines if the device has cycled through 2 steps. If the answer is yes, block 352 increases the intensity I by 2 mA and the method updates the visual display, stores the data in the PCMCIA card and restarts the 20 second timer at block 354. If the answer to decision block 350 is no, block 356 determines if the device has cycled through 3 steps of coarse stimulation. If the answer is yes, block 358 increases the intensity I of the stimulating current by 4 mA and block 354 updates the visual display, stores the data in the PCMCIA card and restarts the 20 second timer. If the answer to decision block 356 is no, block 360 determines that the method is cycling through the fourth step of coarse mode stimulation. Block 362 increases the intensity I of the stimulating current by 6 mA and block 354 updates the visual display, stores the data in the PCMCIA card and restarts the 20 second timer. It should be noted that at block 362 the intensity as increased at STEP 4 cannot be increased above 20 mA. After block 354, the method returns to block 310 and repeats.

With the coarse stimulation mode of the present invention (which includes the signal stability check improvement of the present invention), the user is able to quickly determine if the target tissue area contains the carvernosal nerve to avoid cutting the nerve during the excision or sectioning of tissue. In addition, the coarse mode stimulation method assists in the priming step disclosed in the '331 patent.

Figure 4B:
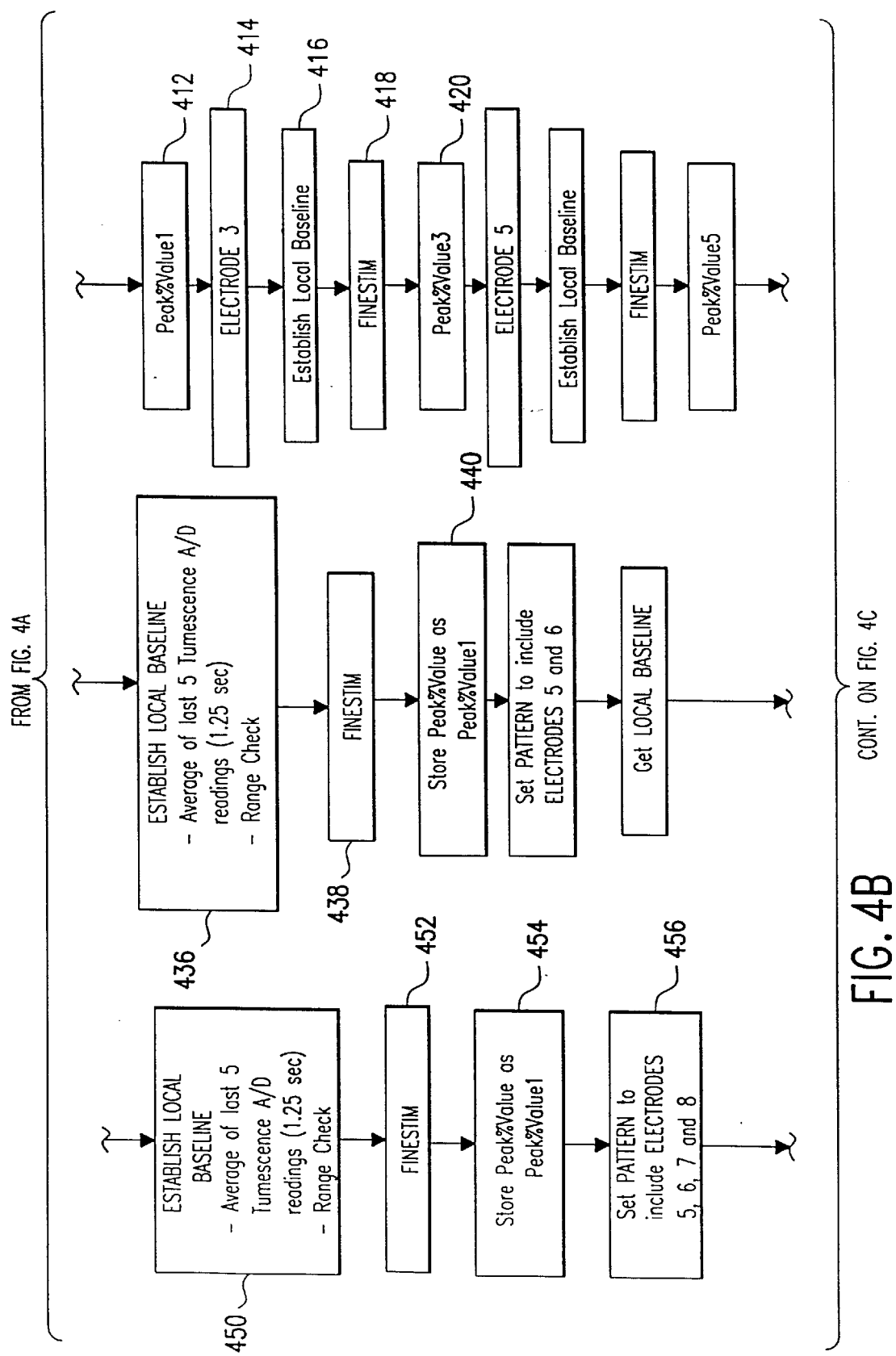
FIG. 4 is a flowchart illustrating a second method for stimulating the nerve known as the "fine" stimulation mode.
Figure 4C:
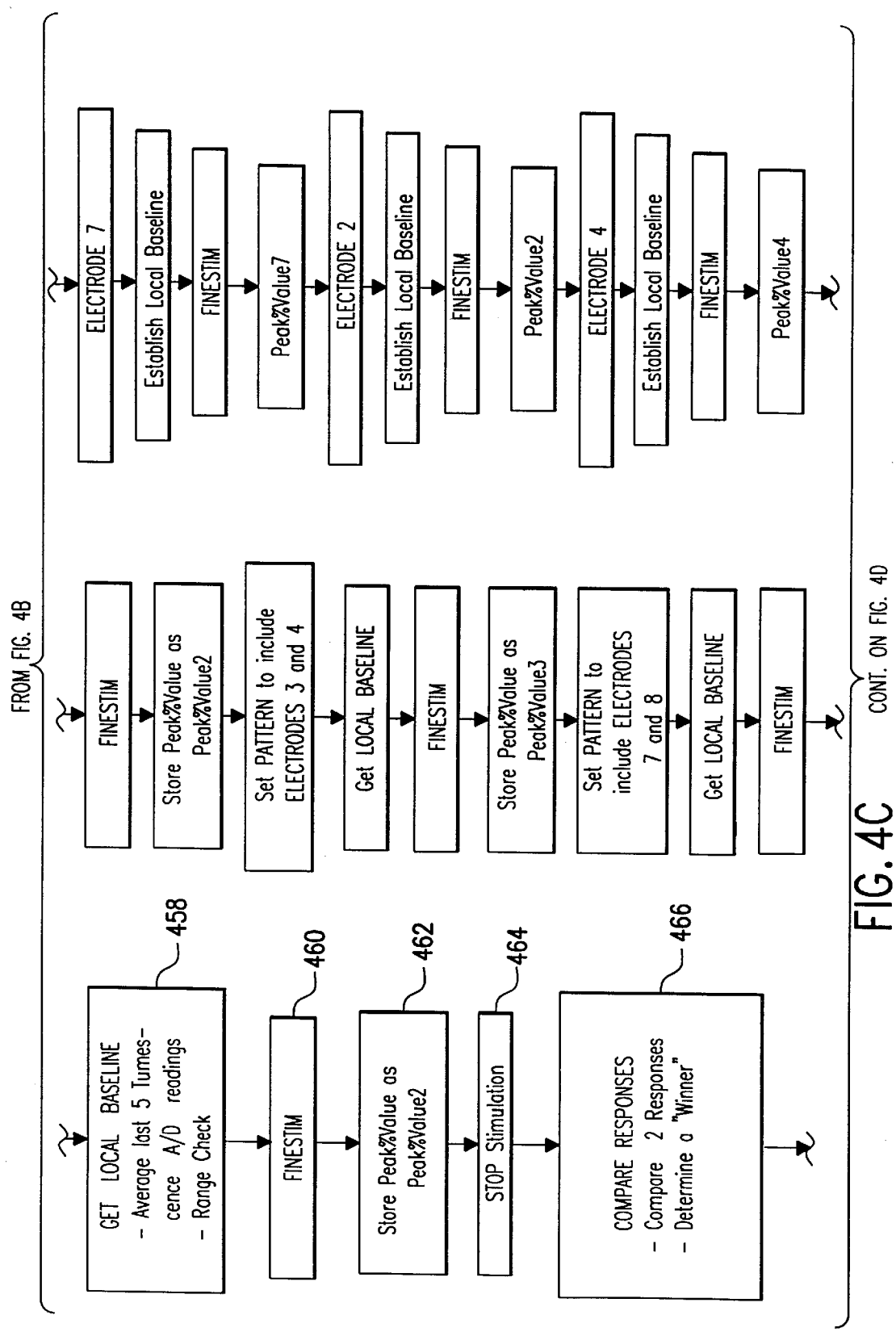
Figure 4D:
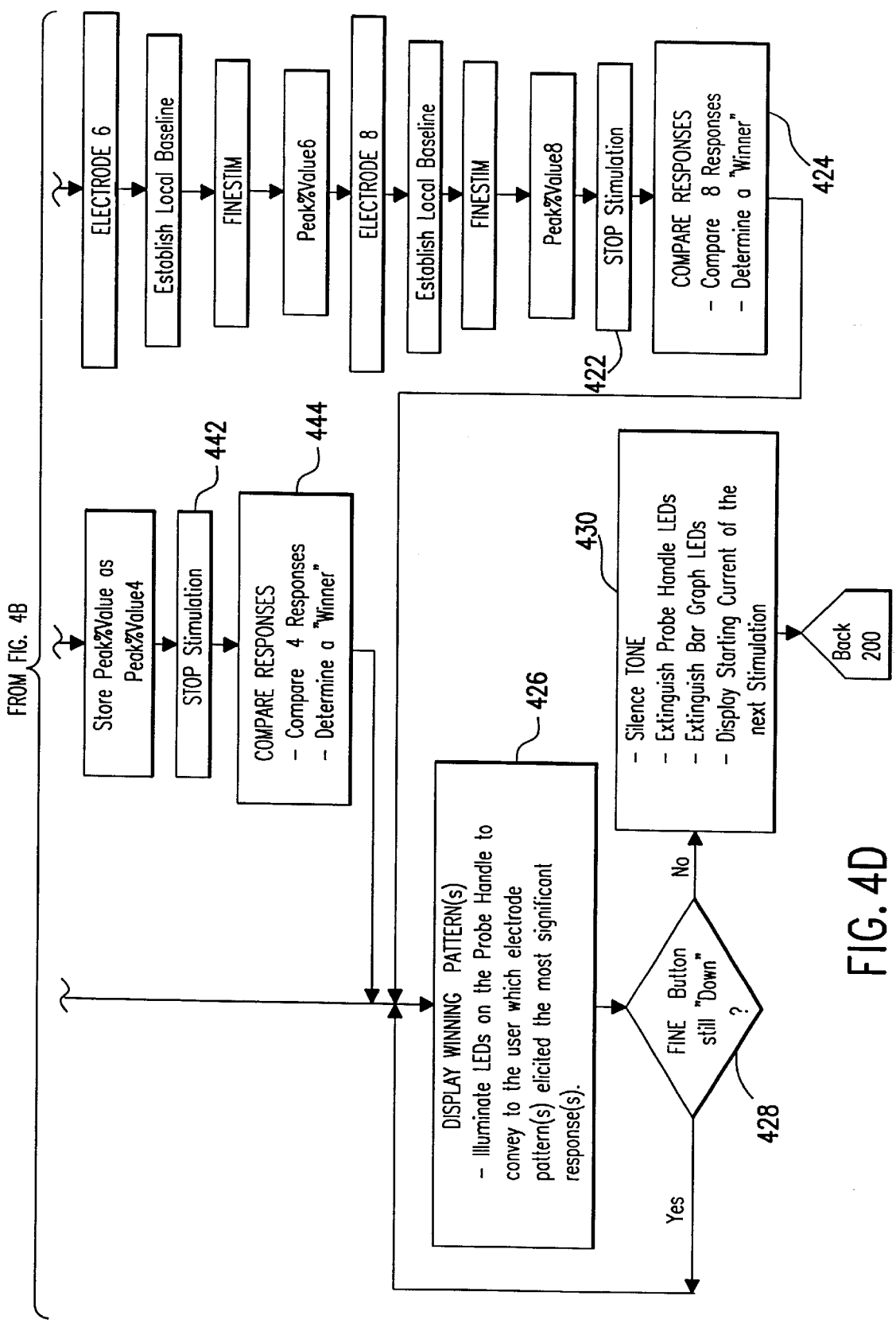
Figure 5A:
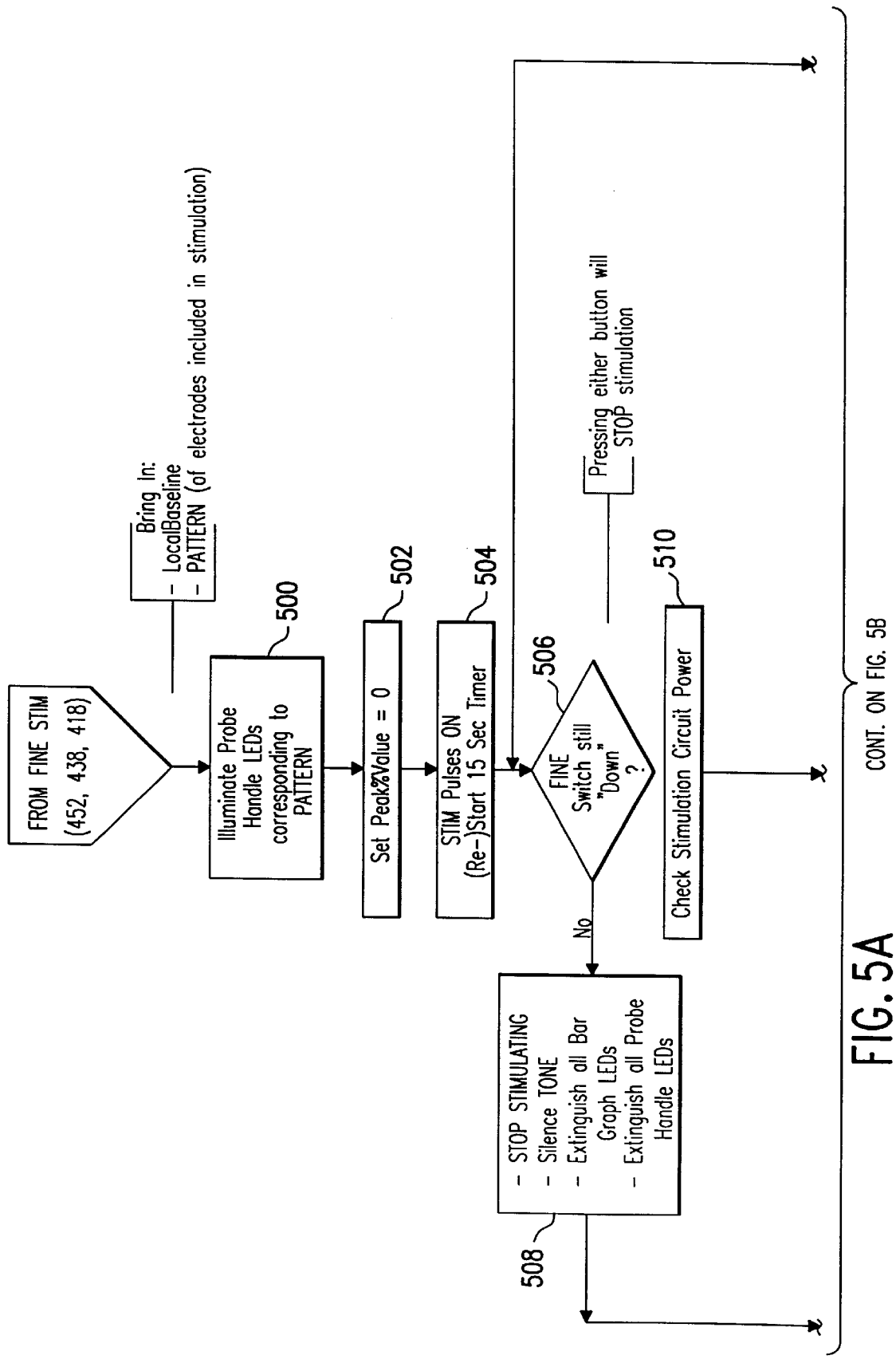
FIG. 5 is a flowchart illustrating the "finestim" step of the method shown in FIG. 4.
Figure 5B:
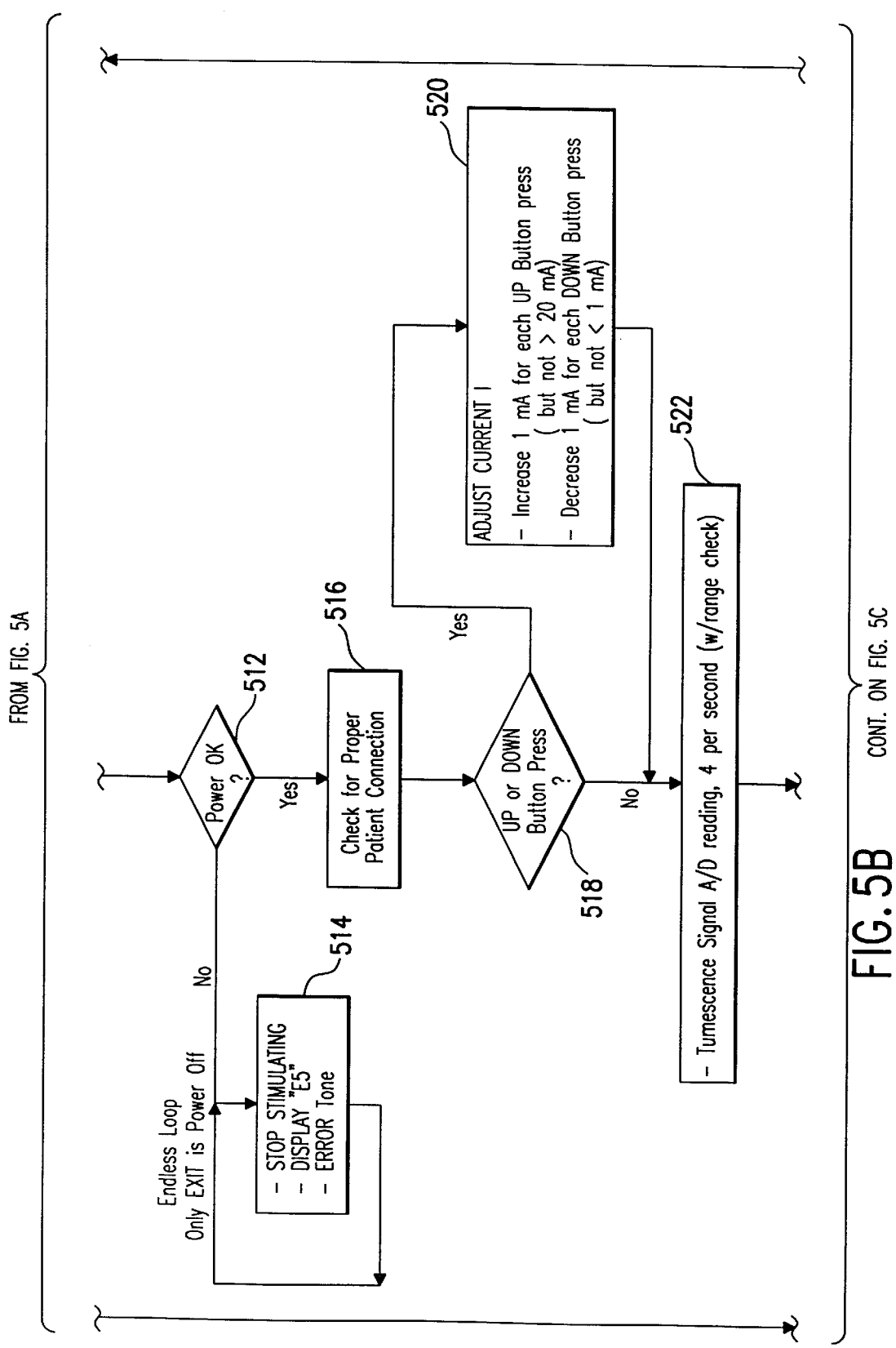
Figure 5C:
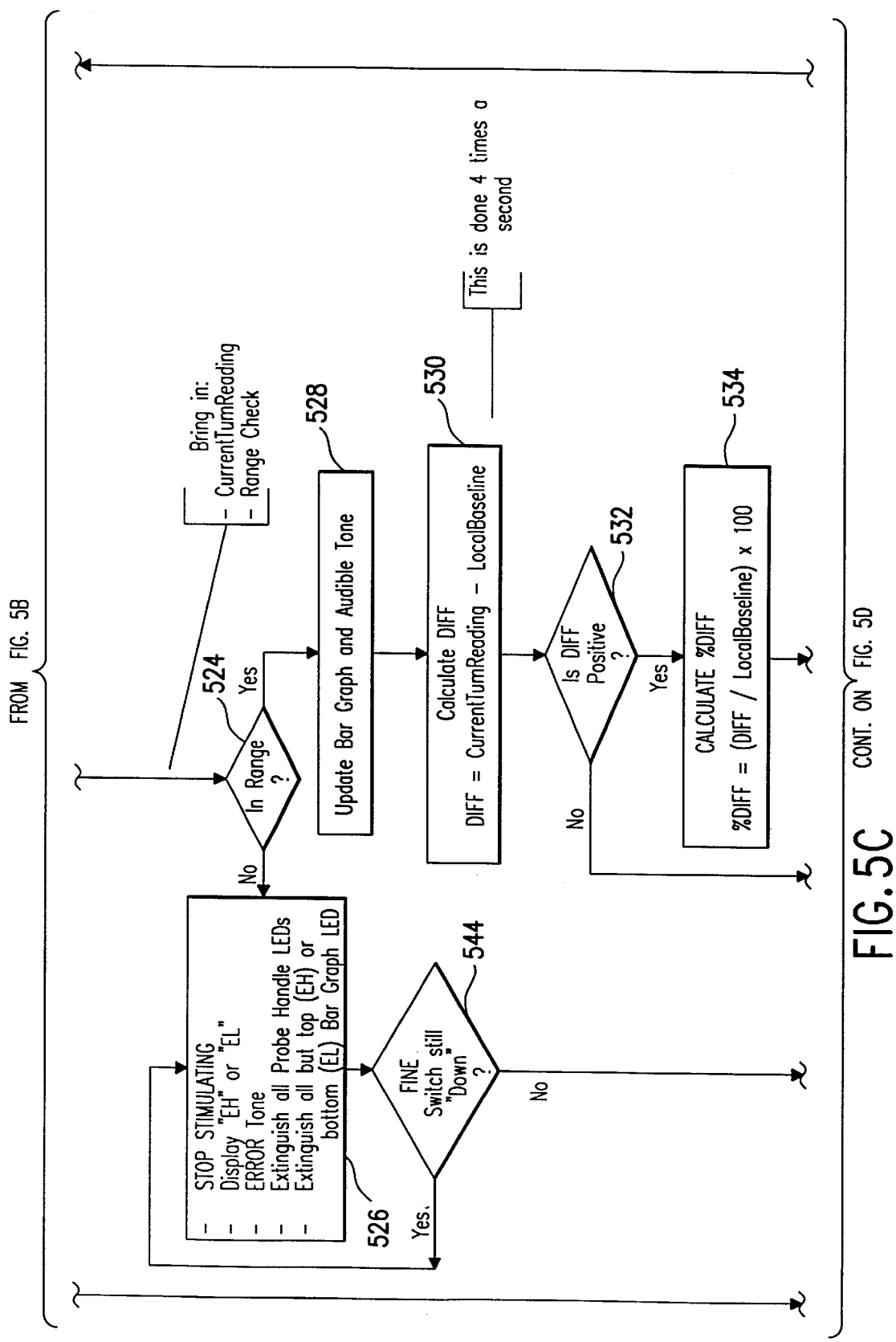
Figure 5D:
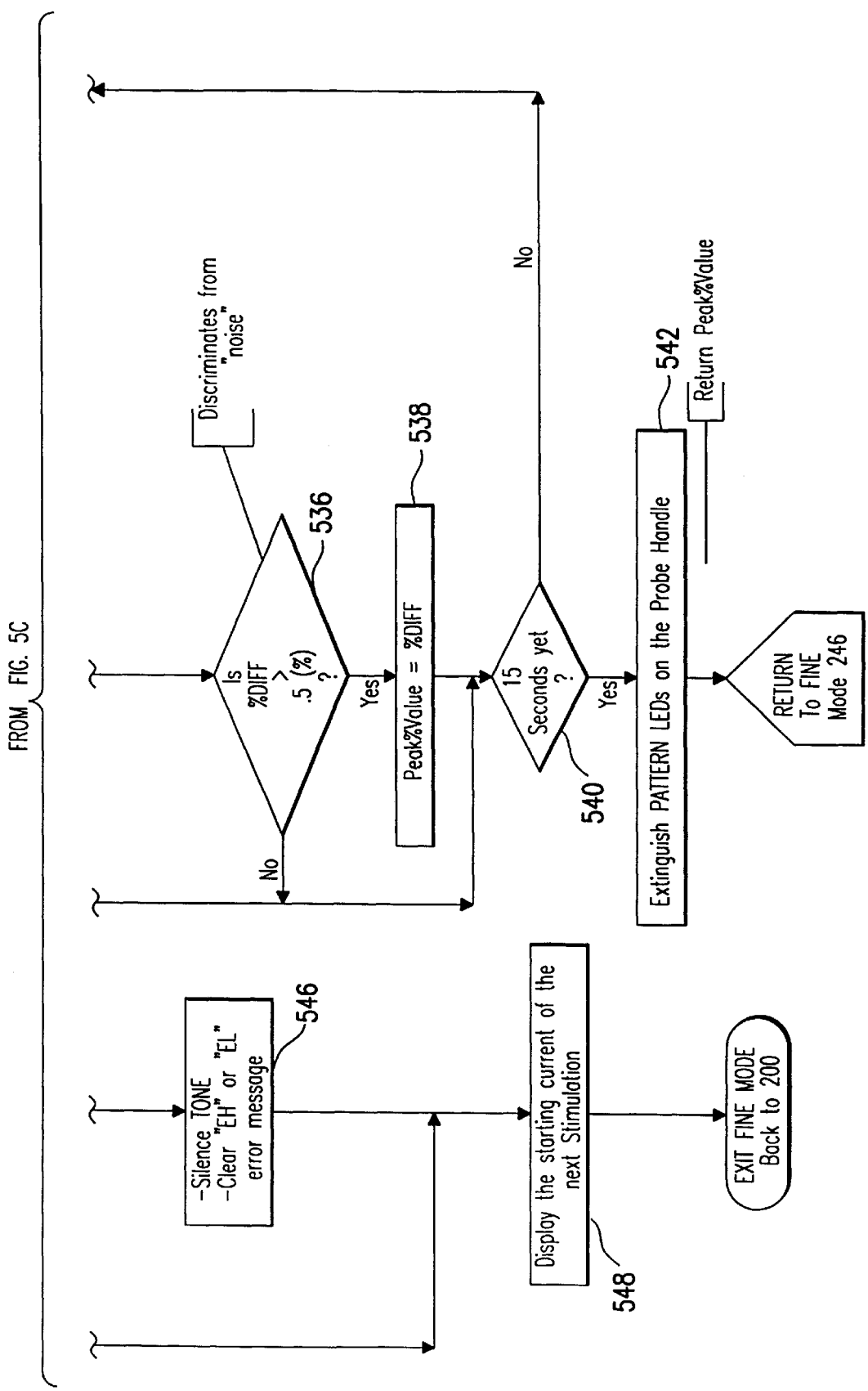

With reference now to FIG. 4, the fine mode method for applying an electro-stimulus to a target tissue area to locate the carvernosal nerve will be described. In general, fine mode stimulation entails applying an electro-stimulus of a constant intensity through 1) each electrode of the probe, 2) four pairs of electrodes, or 3) two sets of four electrodes. The method starts at block 400 which determines if a valid stimulating tip 112 is present. If a valid tip is not present, the method returns to the method of FIG. 2. If the tip is valid, block 402 assesses the user-selected resolution. More particularly, the method establishes whether the method will apply an electro-stimulus through each one of the probe electrodes (resolution 1), through four pairs of electrodes (resolution 2), or through two sets of four electrodes (resolution 4). If resolution 1 is selected, block 404 sets the stimulating current intensity at I. The intensity of the fine mode stimulus current for resolution 1 is 1.5×greater than the coarse mode stimulus current, but not greater than 20 mA. If a PCMCIA datacard is present, the intensity of the stimulus current is stored in the datafile. Block 406 establishes an electro-stimulus for electrode 1 (electrode 1 active). Block 408 establishes a local baseline by averaging the last 5 tumescence signal readings from tumescence monitor 132. Block 410 performs the "finestim" method illustrated in FIG. 5 and described in greater detail below. In general, the finestim method analyzes percent change in a tumescence response evoked by application of the electro-stimulus (and measured and recorded by tumescence monitor 132) to establish a peak percent change value. Block 412 stores the peak percent change from finestim for electrode 1 as peak % value 1. Block 414 establishes an electro-stimulus for electrode 3 (electrode 3 active), while block 416 establishes a tumescence baseline and block 418 performs the finestim method for the electro-stimulus applied by electrode 3. Block 420 stores the peak percent change value from finestim for electrode 3 as peak % value 3. The same three steps are performed for electrodes 5, 7, 2, 4, 6, and 8 and the peak percent change values are stored as peak % value 5, peak % value 7, peak % value 2, peak % value 4, peak % value 6, and peak % value 8, respectively as shown in FIG. 4. After establishing the peak % value for all eight electrodes, stimulation is terminated at block 422. At block 424 each peak % value is compared against the other to determine the "winning" electrode (that is, the electrode responsible for evoking the greatest peak % value). The comparison step generally comprises the step of determining which peak % value represents the greatest peak % value. If the difference between the greatest peak % value and any other peak % value is greater than 0.5% , the electrode responsible for evoking the tumescence response having the greatest peak % value is the "winning" electrode. If the difference between the greatest peak % value and any other peak % value is less than 0.5% , a "tie" between electrodes exists. After determining the winning electrode(s), block 426 illuminates the LED(s) on handle 114 which correspond to the winning electrode(s) to indicate the location of the nerve to the user. Following illumination of the LED(s) corresponding to the winning electrode(s), block 428 determines if the fine button is still down (that is, active). If the answer is yes, the method returns to block 426 and repeats. If the answer is no, block 430 extinguishes all LEDs on the visual display and probe, the audible tone is silenced, and the method returns to block 200 of the method of FIG. 1.

If resolution 2 is selected, block 432 sets the stimulating current intensity at I which is equal to 1.5×the coarse mode stimulus current but is not greater than 20 mA. Block 434 sets a pattern for electrodes 1 and 2, while block 436 establishes a tumescence baseline value and block 438 performs the finestim method for the electro-stimulus applied by electrodes 1 and 2. Block 440 stores the peak percent change value from finestim for electrodes 1 and 2 as peak % value 1. The same three steps are performed for electrodes 5 and 6,3 and 4, and 7 and 8. The peak percent change values are stored as peak % value 2, peak % value 3, and peak % value 4, respectively as shown in FIG. 4. After establishing the peak % value for all four pairs of electrodes, stimulation is terminated at block 442. At block 444 each peak % value is compared against the other to determine the "winning" pair of electrodes in accordance with the comparison method discussed above. Block 426 displays the winning pair or pairs (in the event of a tie) and the method for fine mode stimulation by resolution 2 is completed by blocks 428 and 430.

If resolution 4 is selected, block 446 sets the stimulating current intensity at I which is 1.25×greater than the stimulus intensity for coarse mode stimulation. Block 448 sets a pattern to apply an electro-stimulus through the first set of four electrodes (electrodes 1, 2, 3, 4). Block 450 establishes a tumescence baseline value and block 452 performs the "finestim" method to analyze percent changes in the tumescence response to establish a peak percent change value. Block 454 stores the peak percent change from finestim as peak % value 1. Block 456 sets a pattern to apply an electro-stimulus through the second set of four electrodes (electrodes 5, 6, 7, 8). Block 458 establishes the tumescence baseline value and block 460 performs the finestim method to analyze percent changes in the tumescence response to establish a peak percent change value for the second set of four electrodes. Block 462 stores the peak percent change from block 460 as peak % value 2 and block 464 terminates stimulation. Block 466 compares peak % value 1 and peak % value 2 to determine the winning set of four electrodes. Block 426 displays the winning set on the probe LEDs corresponding to the winning electrodes. Blocks 428 and 430 terminate the fine mode stimulation method in the manner discussed above.

With reference to FIG. 5, the finestim method of the fine mode stimulation of FIG. 4 will be described. The local tumescence baseline and stimulation pattern is brought into the method at block 500 and the LEDs of the probe corresponding to the stimulating pattern from fine mode stimulation are illuminated. The peak % value is set at 0 at block 502. At block 504, the electro-stimulus is delivered to the target tissue area by probe 110 and a 15 second timer is started (or re-started). Decision block 506 determines if the fine stimulation switch is still down (that is, active). If the answer is no, block 508 terminates the stimulation and extinguishes all LEDs on the display and probe. If the answer to decision block 506 is yes, block 510 performs a check of stimulating current circuit 106. Decision block 512 determines if the power is on. If the answer is no, block 514 terminates stimulation and displays an error code. If the answer to block 512 is yes, block 516 checks for a proper patient connection to tumescence monitor 132. Decision block 518 determines if the up/down current intensity switch has been pressed. If the answer is yes, block 520 adjusts the current intensity by 1 mA to a value not greater than 20 mA and not less than 1 mA. Block 522 performs a tumescence signal reading at four readings per second and it performs a tumescence signal range check. Decision block 524 determines if the tumescence signal is in range. If the answer is no, block 526 terminates stimulation, displays an error message and extinguishes the LEDs on the probe and display. If the tumescence signal is in range, the visual and audible displays are updated by block 528. Block 530 calculates the change (differential) in the tumescence signal characterized as a response to the electro-stimulus of block 504. The differential is calculated by subtracting the local baseline tumescence signal reading from the current tumescence response. The step of block 504 is performed 4 times per second. If decision block 532 determines that the differential is positive, the percentage differential is calculated by block 534. (If the differential is not positive, the method advances to block 540). The equation for determining the percentage differential is illustrated in block 534. If block 536 determines that the percentage differential is greater than 0.5% , block 538 stores the percentage differential as the peak % value. If block 540 determines that 15 seconds has elapsed, block 542 extinguishes illumination of the LED pattern on probe 110 and the peak % value is returned to the relevant finestim block of FIG. 4. If the answer to block 540 is no, the method returns to decision block 506 and repeats.

After block 526, block 544 determines if the fine mode stimulation switch is still down. If the answer is yes, the method returns to block 526. If the answer is no, block 546 silences the audible tone and clears the error message. Block 548 displays the intensity of the next electro-stimulus and the method returns to the method of FIG. 1.

With the fine stimulation mode of the invention (including the signal stability check improvement of the invention), the user can determine the location of the carvernosal with improved accuracy and specificity, to avoid cutting the nerve during the excision or sectioning of tissue.

In summary, by continuously monitoring the stability of a tumescence signal prior to application of an electro-stimulus, unstable signals evoked by others factors (such as a change in blood pressure, blood loss, or administration of anesthesia) can be "isolated" from the stimulating method to ensure accurate interpretation of a tumescence response to application of an electro-stimulus. In addition, the device advantageously indicates the stability of the tumescence signal to the user to provide the option of waiting for the signal to stabilize or to proceed with electro-stimulation, if desired.

While the invention has been shown and described with reference to a preferred embodiment, it should be understood by those skilled in the art that modifications to the device and method of the invention can be made without departing from the spirit and scope ofthe invention. For example, although push-button switches have been described, other types of switches are within the scope of the present invention. In addition, instead of displaying the tumescence signal as a digital display, the tumescence signal could be shown graphically on a video monitor with an indication of the history of the tumescence signal. Furthermore, the display could be designed to show the order of change of the tumescence signal, such as a single down arrow to show first order detumescence or two down arrows to show second order detumescence.

The invention is defined by the following claims.

What is claimed is:

1. A device for stimulating and locating a nerve, comprising:

means for detecting and measuring a signal and a change in the signal;

means for determining the stability of the signal provided by said signal detecting and measuring means;

means for applying an electro-stimulus to a plurality of sites within an area of tissue likely to contain the nerve to be located;

means for interpreting the change in the signal evoked by application of an electro-stimulus detected and measured by said detecting and measuring means to determine the location of the nerve;

means for automatically modifying the stimulus application site; and means for indicating the location of the nerve to the user.

2. The device of claim 1, wherein said determining means characterizes the signal as unstable if the signal exhibits a trend value which is greater than one or more predetermined reference values.

3. The device of claim 2 further comprising means to prevent said applying means from applying an electro-stimulus when said determining means has characterized the signal detected and measured by said detecting and measuring means as unstable.

4. The device of claim 3 further comprising means for indicating to the user that said determining means has determined that the signal detected and measured by said detecting and measuring means is unstable.

5. The device of claim 2 further comprising memory for storing a library of predetermined reference values for determining the stability of the signal by said determining means.

6. The device of claim 1 further comprising means for automatically modifying the intensity of the electro-stimulus.

7. The device of claim 1, wherein said automatic modifying means automatically modifies the stimulus application site based on an interpretation of the change in the signal evoked by application of the electro-stimulus.

8. The device of claim 1, wherein said applying means is an array comprising at least one electrode.

9. The device of claim 8, wherein said automatic modifying means automatically modifies the stimulus application site by activating said array of electrodes in accordance with an electrode activating algorithm.

10. A tamescence device for locating the tamescence carvernosal nerve, comprising:

means for detecting and measuring a signal and a change in the signal evoked by application of an electro-stimulus to the carvernosal nerve;

means for analyzing the tamescence signal provided by said detecting and measuring means to determine its stability;

means for applying a stimulus to an area of tissue likely to contain the carvernosal nerve; and means for interpreting the change in the tamescence signal evoked by application of the electro-stimulus to the carvernosal nerve to the determine the location of the nerve.

11. The device of claim 10, wherein said analyzing means characterizes the tamescence signal as unstable if the signal exhibits a trend value which is greater than one or more predetermined reference values.

12. The device of claim 11, further comprising means to prevent said applying means from applying an electro-stimulus when said analyzing means has characterized the tamescence signal detected and measured by said detecting and measuring means as unstable.

13. The device of claim 12 further comprising means for indicating to the user that said analyzing means has determined that the tamescence signal detected and measured by said detecting and measuring means is unstable.

14. The device of claim 11 further comprising memory for storing a library of predetermined reference values for determining the stability of the tamescence signal by said determining means.

15. The device of claim 10 further comprising means for automatically modifying the intensity of the electro-stimulus.

16. The device of claim 10 further comprising an automatic modifying means for automatically modifying the stimulus application site.

17. The device of claim 10, wherein said applying means is an array comprising at least one of electrode.

18. The device of claim 10, wherein said detecting and measuring means is a tumescence monitor comprising distensible tubing.

19. A method for locating the carvernosal nerve, comprising the steps of:

(a) detecting and measuring a tumescence signal;

(b) determining the stability of the tumescence signal and characterizing the signal as stable or unstable;

(c) applying an electro-stimulus to a tissue site likely to contain the carvernosal nerve if it is determined that the tumescence signal is stable;

(d) detecting and measuring a change in the tumescence signal evoked by application of the electro-stimulus; and (e) interpreting the change in the tumescence signal evoked by application of the electro-stimulus signal.

20. The method of claim 19, wherein the tumescence signal of step (a) is characterized as unstable if a contrast value of the signal is greater than a corresponding predetermined critical contrast value.

21. The method of claim 19, wherein said step of determining the stability of the signal comprises a mathematical, multi-order analysis.

22. The method of claim 19, wherein if said determining step determines that the tumescence signal is unstable, steps (a) and (b) are repeated until the determining step determines that the tumescence signal is stable.

23. The method of claim 19 further comprising the step of:

(f) automatically modifying the stimulus application site based on the interpretation of the change in the tumescence signal.

24. The method of claim 23 further comprising the step of repeating steps (c)–(f) until the carvernosal nerve is located.

25. The method of claim 23 further comprising the step of indicating the location of the carvernosal nerve.

26. The method of claim 19 further comprising the step of indicating when said determining step has determined that the tumescence signal is unstable.

27. A method for locating a nerve, comprising the steps of:

(a) detecting and measuring a signal from a nerve fiber, organ or muscle;

(b) determining the stability of the signal and characterizing it as stable or unstable;

(c) applying an electro-stimulus to a tissue site likely to contain the nerve if it is determined that the signal is stable;

(d) detecting and measuring a change in the signal due to application of the electro-stimulus; and (e) interpreting the change in the signal evoked by application of the electro-stimulus.

28. The method of claim 27, wherein the signal of step (a) is characterized as unstable if a contrast value of the signal is greater than a corresponding predetermined critical contrast value.

29. The method of claim 28 further comprising the step of:

(f) automatically modifying the intensity of the electro-stimulus application site based on the interpretation of change in the signal.

30. The method of claim 29 further comprising the step of repeating steps (c)–(f) until the nerve is located.

31. The method of claim 30 further comprising the step of indicating the location of the nerve.

32. The method of claim 28 further comprising the step of indicating when said determining step has determined that the signal is unstable.

33. The method of claim 27, wherein said step of determining the stability of the signal comprises a mathematical, multi-order analysis.

34. The method of claim 27, wherein if said determining step determines that the signal is unstable, steps (a) and (b) are repeated until the determining step determines that the signal is stable.

35. A method for determining the stability of a signal from a nerve fiber, organ or muscle, comprising the step of recording and analyzing a contrast value of the signal at discrete intervals.

36. The method of claim 35, wherein the step is repeated until the signal is determined to be stable.

37. The method of claim 35, wherein the analysis is a mathematical, multiorder analysis.

\* \* \* \* \*